(12) United States Patent
Morf et al.

(10) Patent No.: US 10,444,378 B1
(45) Date of Patent: Oct. 15, 2019

(54) IMAGING DEVICES

(71) Applicant: Varian Medical Systems, Inc., Palo Alto, CA (US)

(72) Inventors: Daniel Morf, Buch am Irchel (CH); Josh Star-Lack, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/964,639

(22) Filed: Apr. 27, 2018

(51) Int. Cl.
| | |
|---|---|
| *G01T 1/24* | (2006.01) |
| *G01T 1/20* | (2006.01) |
| *H01L 25/065* | (2006.01) |
| *A61B 6/00* | (2006.01) |
| *H01L 27/146* | (2006.01) |
| *G21K 4/00* | (2006.01) |

(52) U.S. Cl.
CPC .......... *G01T 1/2018* (2013.01); *A61B 6/4035* (2013.01); *G01T 1/2008* (2013.01); *G01T 1/241* (2013.01); *G01T 1/242* (2013.01); *G21K 4/00* (2013.01); *H01L 25/0655* (2013.01); *H01L 27/1464* (2013.01); *H01L 27/14636* (2013.01); *H01L 27/14658* (2013.01); *H01L 27/14663* (2013.01)

(58) Field of Classification Search
CPC ..... G01T 1/2008; G01T 1/2018; G01T 1/241; G01T 1/242; G21K 4/00; G21K 2004/04; A61B 6/4035; H01L 27/14632; H01L 27/14663; H01L 27/1464; H01L 27/14636; H01L 25/0655; H01L 27/14658
See application file for complete search history.

(56) References Cited

U.S. PATENT DOCUMENTS

| | | | | |
|---|---|---|---|---|
| 6,472,665 | B1* | 10/2002 | Ishisaka ................ | G01T 1/2018 250/368 |
| 2005/0051447 | A1* | 3/2005 | Nakajo .................. | G03B 42/04 206/455 |
| 2006/0151708 | A1* | 7/2006 | Bani-Hashemi ...... | G01T 1/2008 250/370.11 |
| 2008/0245968 | A1* | 10/2008 | Tredwell ............... | G01T 1/2018 250/370.09 |

(Continued)

OTHER PUBLICATIONS

Menge et al., "Performance of large lanthanum bromide scintillators," 2007, Nuclear Instruments and Methods in Physics Research A, vol. 579, pp. 6-10. (Year: 2007).*

(Continued)

*Primary Examiner* — Kiho Kim
(74) *Attorney, Agent, or Firm* — Vista IP Law Group, LLP (57) ABSTRACT

An imaging device includes: a first scintillator layer; an array of detector elements, wherein the array of detector elements comprises a first detector element; a second scintillator layer, wherein the array of detector elements is located between the first scintillator layer and the second scintillator layer; and a first neutral density filter located between the first scintillator layer and the first detector element and/or a second neutral density filter located between the second scintillator layer and the first detector element; wherein the first detector element is configured to generate a first electrical signal in response to light from the first scintillator layer, and to generate a second electrical signal in response to light from the second scintillator layer.

32 Claims, 4 Drawing Sheets

(56) References Cited

U.S. PATENT DOCUMENTS

| | | | |
|---|---|---|---|
| 2009/0152563 A1* | 6/2009 | Hayashi | H01L 27/14609 257/72 |
| 2009/0250619 A1* | 10/2009 | Nakamura | H01L 27/14665 250/370.09 |
| 2010/0320391 A1* | 12/2010 | Antonuk | H01L 27/1462 250/366 |
| 2012/0097858 A1 | 4/2012 | Morf | |
| 2014/0167046 A1* | 6/2014 | Shieh | H01L 27/1225 257/53 |

OTHER PUBLICATIONS

International Search Report and Written Opinion dated May 31, 2019 for corresponding PCT Application No. PCT/US2019/029464.

* cited by examiner

IMAGING DEVICES

FIELD

The field of the application relates to imaging devices, and more particularly to medical imaging devices.

BACKGROUND

Imaging devices, such as an x-ray imager, have been used for diagnostic and treatment purposes. One type of x-ray imager is a diagnostic imager configured to operate with a diagnostic radiation source. Another type of x-ray imager is a high DQE detector that is configured for use with a treatment radiation source. An x-ray imager may also be configured for use with both diagnostic radiation beam and treatment radiation beam.

Creating a high DQE detector for portal imaging presents a significant technical challenge. One approach uses thick pixilated scintillator arrays that are coupled to an electronic portal imaging device (EPID). Incoming x-ray photons deposit energy into the scintillators which then produce optical photons via luminescence. These optical photons, which originate with random polarizations and direction vectors after the luminescence events, are transported throughout the scintillator during which time they can be reflected, refracted and scattered. Eventually, many photons will cross the boundary between the scintillator and the photodiode array to be absorbed by the EPID's photodiodes and converted into electrical current for readout and digitization. Despite the promise of the technology, performance may be inadequate and a significant manufacturing cost lies in the process of cutting the crystalline scintillators into parallelepipeds and gluing reflective septa between them in order to reduce optical cross talk.

Also, in some cases, an x-ray imager (e.g., a diagnostic x-ray imager or a portal imager) may comprise a scintillator coupled to a photodiode array. X-ray photons deposit energy into the scintillator thereby producing optical photons with random direction and polarization vectors. A percentage of these optical photons will cross the scintillator-photodiode boundary and deposit energy. The photodiodes convert optical photons into electron-hole pairs. After a sufficient amount of charge is collected, signals are read out and digitized to form an image. To achieve a sufficiently high spatial resolution, optical blurring is desired to be minimized. This implies that the photodiode signals associated with a given x-ray photon should be localized in close lateral proximity to where that x-ray photon interacted with the scintillator. A common means of achieving this goal is through the use of pixelated geometries that confine optical photons using reflective septa. Unfortunately, this approach suffers from high manufacturing costs and may not be practical for incorporating into large-area imagers. As similarly discussed, the process of cutting the crystalline scintillators (e.g. CsI, CdWO4, BGO) into parallelepipeds, gluing reflective septa between them, and then assembling the pixels into a complete array, may be very expensive. Another disadvantage of the pixelated geometry is the loss of fill factor (and associated quantum efficiency) due to the finite thickness of the septa.

Also, current amorphous silicon based flat panel imagers for megavoltage radiation suffers from very low x-ray conversion efficiency. Only about 1.3% of the x-ray photons contribute to an image. In other words, more than 98% of the imaging dose gets lost and will not contribute to the image formation. Approaches that utilize thicker scintillator are either very expensive because the scintillator has to be pixelated or has to exhibit very high imaging performance due to added blurring.

SUMMARY

An imaging device includes: a first scintillator layer; an array of detector elements, wherein the array of detector elements comprises a first detector element; a second scintillator layer configured to receive radiation after the radiation has passed through the first scintillator layer and the array of detector elements, wherein the array of detector elements is located between the first scintillator layer and the second scintillator layer; a first electrode located closer to the first scintillator than the second scintillator; and a second electrode situated between the second scintillator and the first detector element; wherein the first detector element is configured to generate a first electrical signal in response to light from the first scintillator layer, and to generate a second electrical signal in response to light from the second scintillator layer; and wherein the second electrode is configured to allow the light from the second scintillator layer to reach the first detector element.

Optionally, the first electrode is situated between the first scintillator and the first detector element, and wherein the first electrode is configured to allow light from the first scintillator layer to reach the first detector element.

Optionally, the second electrode is made from a non-transparent conductive material but is etched with a pattern to allow light to pass therethrough.

Optionally, the second electrode has a polygonal pattern.

Optionally, the first detector element has a first part configured to generate the first electrical signal in response to the light from the first scintillator layer, and a second part configured to generate the second electrical signal in response to the light from the second scintillator layer.

Optionally, the first part is a top side of the first detector element, and the second part is a bottom side of the first detector element.

Optionally, the first part comprises a first photodiode, and the second part comprises a second photodiode, and wherein the first photodiode and the second photodiode form a side-by-side configuration.

Optionally, the second electrode is at least partially transparent to light.

Optionally, the second electrode comprises a first opening for allowing the light from the second scintillator layer to pass therethrough.

Optionally, the second electrode comprises a second opening.

Optionally, the first opening comprises a circular opening, a square opening, a rectangular opening, or a slot.

Optionally, the second electrode has a ring configuration.

Optionally, the second electrode has a grid configuration, and the first opening is one of a plurality of grid holes.

Optionally, the second electrode comprises a chrome layer.

Optionally, the second electrode comprises ITO or another transparent conductor.

Optionally, the first detector element comprises a hardware component, and wherein the second electrode and the hardware component are in a side-by-side configuration.

Optionally, the second electrode comprises a conductor extending along at least a part of a periphery of the second electrode, and one or more optical openings surrounded by the periphery.

Optionally, the hardware component comprises at least a part of a thin-film-transistor (TFT)

Optionally, the second electrode further comprises one or more additional conductors extending within a space that is surrounded by the periphery of the second electrode.

Optionally, the imaging device further includes a substrate, wherein the array of detector elements is secured to the substrate, wherein the substrate has a first side and an opposite second side, the first side being closer to a radiation source than the second side.

Optionally, the array of detector elements is located closer to the first side of the substrate than the second side, or vice versa.

Optionally, a first part of the first detector element is located closer to the first side of the substrate than the second side.

Optionally, the substrate has a thickness that is less than 2 mm.

Optionally, the imaging device further includes a layer of focusing elements located between (1) the array of detector elements and (2) the first scintillator layer or the second scintillator layer.

Optionally, the first scintillator layer is non-pixelated, the second scintillator layer is non-pixelated, or both the first and second scintillator layers are non-pixelated.

Optionally, one or both of the first and second scintillator layers are pixelated.

Optionally, the imaging device further includes an optical grid coupled to the first scintillator layer or the second scintillator layer.

Optionally, the imaging device further includes a first optical grid coupled to the first scintillator layer, and a second optical grid coupled to the second scintillator layer.

Optionally, the imaging device further includes a first plate coupled to the first scintillator layer, and a second plate coupled to the second scintillator layer, wherein both the first scintillator layer and the second scintillator layer are between the first and second plates.

Optionally, the imaging device further includes a first neutral density filter located between the first scintillator layer and the first detector element and/or a second neutral density filter located between the second scintillator layer and the first detector element.

Optionally, the first neutral density filter and/or the second neutral density filter is configured to improve a signal-to-noise ratio of the imaging device.

Optionally, a signal-to noise ratio of the imaging device is based on (1) respective quantum efficiencies (QE1,QE2) of the first and second scintillator layers, (2) respective detective quantum efficiencies (DQE1,DQE2) of the first and second scintillator layers, (3) respective optical yields (☐☐☐☐☐☐☐of the first and second scintillator layers, (4) optical sensitivities (p1, p2) of the first detector element associated with the first and second scintillators respectively, or (5) a combination of any of the foregoing.

Optionally, the first electrical signal has a first feature value (e1), and the second electrical signal has a second feature value (e2); and wherein min (e1, e2)/max (e1, e2) is larger than a threshold.

Optionally, the first feature value (e1) is a function of quantum efficiency QE1 of the first scintillator layer, optical yield☐☐☐ of the first scintillator layer, and optical sensitivity p1 of the first detector element associated with the first scintillator layer; and wherein the second feature value (e2) is a function of quantum efficiency QE2 of the second scintillator layer, optical yield☐☐☐ of the second scintillator layer, and optical sensitivity p2 of the first detector element associated with the second scintillator layer.

Optionally, the first feature value (e1) is a function of detective quantum efficiency DQE1 of the first scintillator layer, optical yield☐☐☐ of the first scintillator layer, and optical sensitivity p1 of the first detector element associated with the first scintillator layer; and wherein the second feature value (e2) is a function of detective quantum efficiency DQE2 of the second scintillator layer, optical yield☐☐☐ of the second scintillator layer, and optical sensitivity p2 of the first detector element associated with the second scintillator layer.

Optionally, the threshold is larger than 0.5.

Optionally, the threshold is larger than 0.7.

An imaging device includes: a first scintillator layer; an array of detector elements, wherein the array of detector elements comprises a first detector element; a second scintillator layer, wherein the array of detector elements is located between the first scintillator layer and the second scintillator layer; and a first neutral density filter located between the first scintillator layer and the first detector element and/or a second neutral density filter located between the second scintillator layer and the first detector element; wherein the first detector element is configured to generate a first electrical signal in response to light from the first scintillator layer, and to generate a second electrical signal in response to light from the second scintillator layer.

Optionally, the first neutral density filter and/or the second neutral density filter is configured to improve a signal-to-noise ratio of the imaging device.

Optionally, a signal-to noise ratio of the imaging device is based on (1) respective quantum efficiencies (QE1,QE2) of the first and second scintillator layers, (2) respective detective quantum efficiencies (DQE1,DQE2) of the first and second scintillator layers, (3) respective optical yields (☐☐☐☐☐☐☐of the first and second scintillator layers, (4) optical sensitivities (p1, p2) of the first detector element associated with the first and second scintillators respectively, or (5) a combination of any of the foregoing.

Optionally, the first electrical signal has a first feature value (e1), and the second electrical signal has a second feature value (e2); and wherein the first neutral density filter and/or the second neutral density filter is configured such that min (e1, e2)/max (e1, e2) is larger than a threshold.

Optionally, the first feature value (e1) is a function of quantum efficiency QE1 of the first scintillator layer, optical yield☐☐☐ of the first scintillator layer, and optical sensitivity p1 of the first detector element associated with the first scintillator layer; and wherein the second feature value (e2) is a function of quantum efficiency QE2 of the second scintillator layer, optical yield☐☐☐ of the second scintillator layer, and optical sensitivity p2 of the first detector element associated with the second scintillator layer.

Optionally, the first feature value (e1) is a function of detective quantum efficiency DQE1 of the first scintillator layer, optical yield☐☐☐ of the first scintillator layer, and optical sensitivity p1 of the first detector element associated with the first scintillator layer; and wherein the second feature value (e2) is a function of detective quantum efficiency DQE2 of the second scintillator layer, optical yield☐☐☐ of the second scintillator layer, and optical sensitivity p2 of the first detector element associated with the second scintillator layer.

Optionally, the threshold is larger than 0.5.

Optionally, the threshold is larger than 0.7.

Optionally, the second scintillator layer is configured to receive radiation after it has passed through the array of detector elements.

Optionally, the imaging device further includes a first electrode situated between the first scintillator and the first detector element, wherein the first electrode is configured to allow light from the first scintillator layer to reach the first detector element.

Optionally, the imaging device further includes a second electrode configured to allow the light from the second scintillator layer to reach the first detector element.

Optionally, the first detector element has a first part configured to generate the first electrical signal in response to the light from the first scintillator layer, and a second part configured to generate the second electrical signal in response to the light from the second scintillator layer.

Optionally, the first part is a top side of the first detector element, and the second part is a bottom side of the first detector element.

Optionally, the first part comprises a first photodiode, and the second part comprises a second photodiode, and wherein the first photodiode and the second photodiode form a side-by-side configuration.

Optionally, the second electrode is at least partially transparent to light.

Optionally, the second electrode comprises a first opening for allowing the light from the second scintillator layer to pass therethrough.

Optionally, the second electrode comprises a second opening.

Optionally, the first opening comprises a circular opening, a square opening, a rectangular opening, or a slot.

Optionally, the second electrode has a ring configuration.

Optionally, the second electrode has a grid configuration, and the first opening is one of a plurality of grid holes.

Optionally, the second electrode comprises a chrome layer.

Optionally, the second electrode comprises ITO or another transparent conductor.

Optionally, the first detector element comprises a hardware component, and wherein the second electrode and the hardware component are in a side-by-side configuration.

Optionally, the second electrode comprises a conductor extending along at least a part of a periphery of the second electrode, and one or more optical openings surrounded by the periphery.

Optionally, the second electrode further comprises one or more additional conductors extending within a space that is surrounded by the periphery of the second electrode.

Optionally, the hardware component comprises at least a part of a thin-film-transistor (TFT).

Optionally, the imaging device further includes a substrate, wherein the array of detector elements is secured to the substrate, wherein the substrate has a first side and an opposite second side, the first side being closer to a radiation source than the second side.

Optionally, the imaging device further includes a layer of focusing elements located between (1) the array of detector elements and (2) the first scintillator layer or the second scintillator layer.

Optionally, the imaging device further includes an optical grid coupled to the first scintillator layer or the second scintillator layer.

Optionally, the imaging device further includes a first optical grid coupled to the first scintillator layer, and a second optical grid coupled to the second scintillator layer.

Optionally, the imaging device further includes a first plate coupled to the first scintillator layer, and a second plate coupled to the second scintillator layer, wherein both the first scintillator layer and the second scintillator layer are between the first and second plates.

Optionally, the substrate has a thickness that is less than 2 mm.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 1:
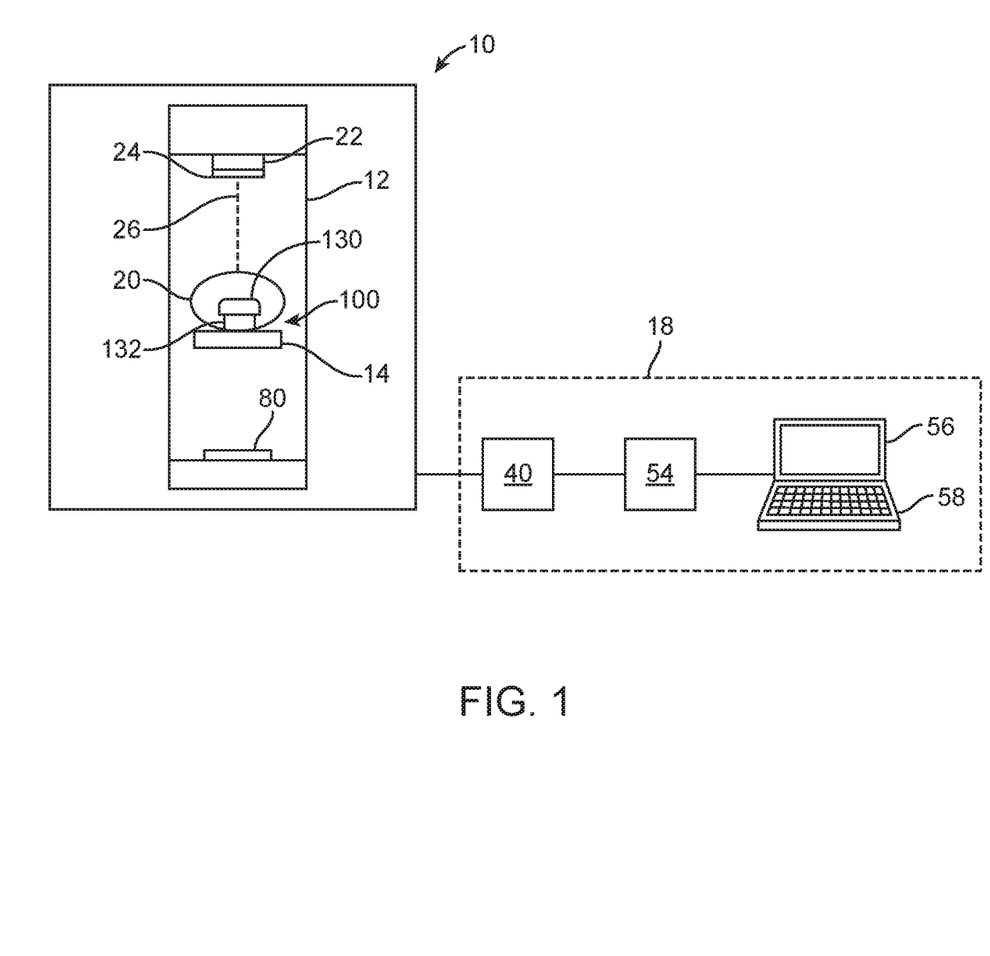
FIG. 1 illustrates a radiation system having an imaging device in accordance with some embodiments.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam, electron beam, or photon beam, as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purposes. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). Also, in some embodiments, the imager 80 may be a portal imager configured to perform portal imaging. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels. In some embodiments, the radiation source 22 is able to generate X-ray radiation at a plurality of photon energy levels. For example, the accelerator may have an energy range from 1 MV to 20 MV, producing an x-ray having a range from 10 kV to 160 kV. In other cases, the energy may have a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2:
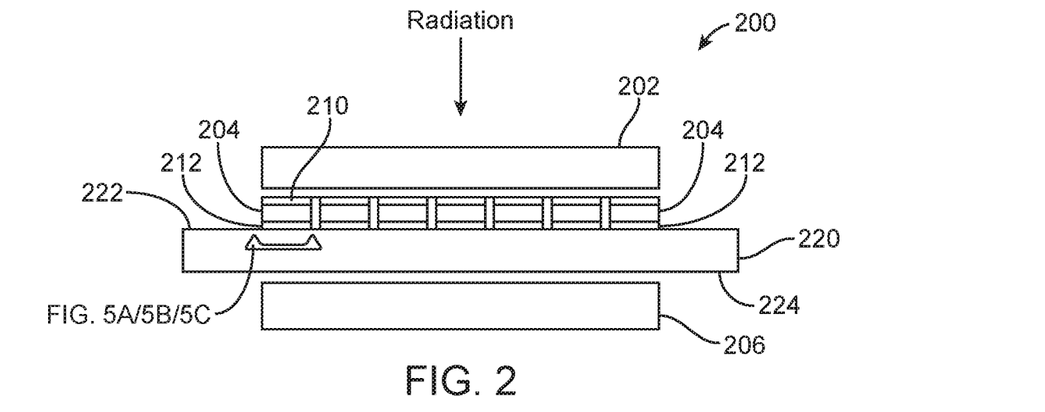
FIG. 2 illustrates an imaging device in accordance with some embodiments.

The imager 80 may have different configurations in different embodiments. FIG. 2 illustrates an imaging device 200 in accordance with some embodiments. The imaging device 200 may be used to implement the imager 80 in some embodiments. As shown in the figure, the imaging device 200 includes a first scintillator layer 202, and an array of detector elements 204. In some embodiments, each detector element 204 may include one or more amorphous silicon (a:Si) detector. The imaging device 200 also includes a second scintillator layer 206. As shown in the figure, the array of detector elements 204 is located between the first scintillator layer 202 and the second scintillator layer 206. The second scintillator layer 206 is configured to receive radiation after it has passed through the array of detector elements 204. The imaging device 200 also includes electrodes 210, 212 coupled to respective ones of the detector elements 204. Each detector element 204 is configured to generate a first electrical signal in response to light from the first scintillator layer 202, and to generate a second electrical signal in response to light from the second scintillator layer 206.

In the illustrated embodiments, each detector element 204 has a first electrode 210 electrically coupled thereto, and a second electrode 212 coupled thereto. The first electrode 210 and the second electrode 212 are on opposite sides of the detector element 204, and are configured to receive opposite charge of an electron-hole pair generated in the detector element 204 in response to detected light. In the illustrated embodiments, the second electrode 212 has a configuration for allowing the light from the second scintillator layer 206 to reach the detector element 204. Also, in some embodiments, the first electrode 210 also has a configuration for allowing light from first scintillator layer 202 to reach the detector element 204. In some embodiments, the detector element 204 may be implemented using a photodiode. Also, in some embodiments, the electrodes 210, 212 may be considered as parts of the photodiode, or as terminals that are separately coupled to the photodiode.

Figure 3:
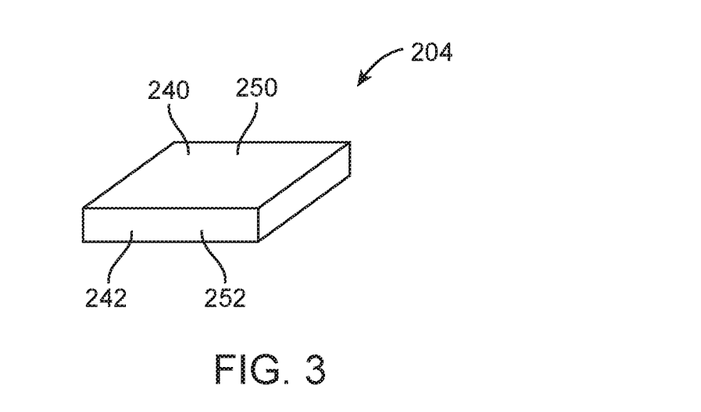
FIG. 3 illustrates a detector element in accordance with some embodiments.
Figure 4:
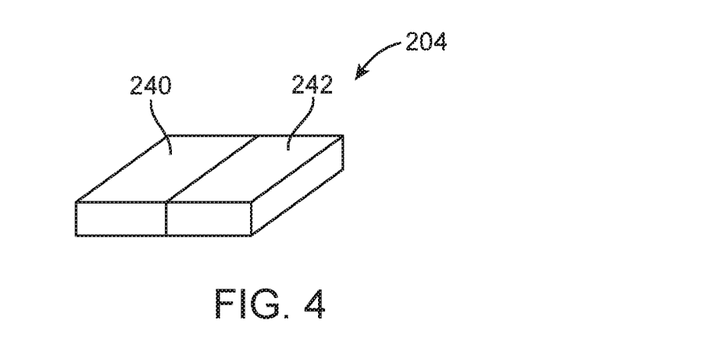
FIG. 4 illustrates another detector element in accordance with other embodiments.

In some embodiments, the detector element 204 has a first part configured to generate a first electrical signal in response to the light from the first scintillator layer 202, and a second part configured to generate a second electrical signal in response to the light from the second scintillator layer 206. In some cases, the first part 240 is a top side 250 of the detector element 204, and the second part 242 is a bottom side 252 of the detector element 204 (FIG. 3). In other cases, the first part 240 and the second part 242 may form a side-by-side configuration (FIG. 4).

Also, in some embodiments, the first part may comprise a first photodiode element, and the second part may comprise a second photodiode element. In this specification, the term "photodiode element" refers to one or more electrical circuit element(s) on a detector pixel that are associated with converting photon energy into electrical signals. This can include, but is not limited to, photodiode(s), switching transistor(s), amplification transistor(s), direct conversion element, or a combination thereof. The first scintillator layer 202 and the second scintillator layer 206 are configured to receive radiation and generate photons in response to the radiation. The first photodiode element is configured to generate electrical signals in response to the photons provided from the first scintillator layer 202, and the second photodiode element is configured to generate electrical signals in response to photons provided from the second scintillator layer 206. The electrical signals are then read out and digitized to form an image. In some embodiments, a circuit is provided to combine the signals from the first and second photodiode elements for each detector element 204 to form each pixel in the image.

Figure 5A:
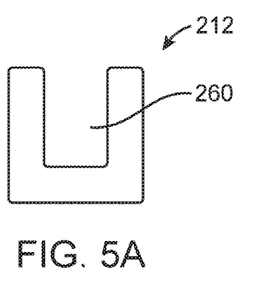
FIGS. 5A-5E illustrates examples of an electrode in different embodiments.
Figure 5B:
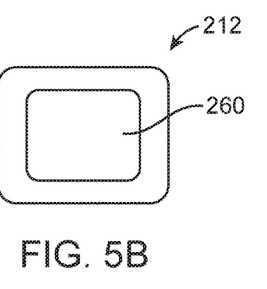
Figure 5C:
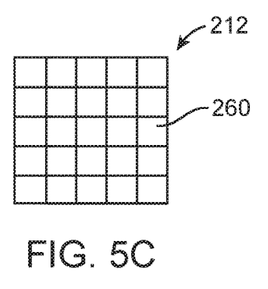
Figure 5D:
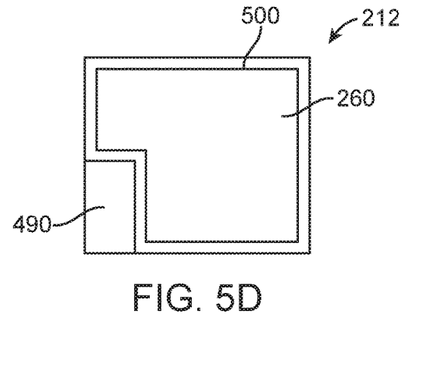
Figure 5E:
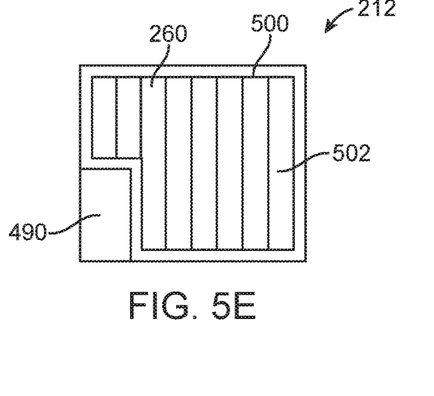

In the illustrated embodiments, the electrode 212 is at least partially transparent to light. In some cases, the electrode 212 may comprise a first opening 260 for allowing the light from the second scintillator layer 206 to pass therethrough (FIG. 5A). Also, in some embodiments, the electrode 212 may comprise multiple openings (e.g., a first opening and a second opening) for allowing light from the second scintillator layer 206 to pass therethrough. The first opening may comprise a circular opening, a square opening, a rectangular opening, or a slot. In some embodiments, the electrode 212 may have a ring configuration (FIG. 5B). In further embodiments, the electrode 212 may have a grid configuration, and the opening 260 is one of a plurality of grid holes (FIG. 5C). In some embodiments, the electrode 212 may have a shape that accommodates component(s) of the detector element 204, such as that shown in FIG. 5D. As shown in the figure, the electrode 212 has a substantially square shape that accommodates component(s) 490 of the detector element 204 at the corner or side(s) of the electrode 212. The component(s) 490 may be photodiode, or hardware component(s) (such as at least a part of a thin-film-transistor (TFT), trace, wire, circuit, etc.). In other embodiments, the electrode 212 may have a rectangular shape, a circular shape, a hexagonal shape, or other customized shapes. The electrode 212 is positioned next to the component(s) 490 of the detector element 204 in a side-by-side configuration, and defines the opening 260 for allowing light to travel therethrough. In some embodiments, the opening 260 may be a space without any material. In other embodiments, the opening 260 may be filled or covered by an optically transparent material, which may or may not be electrically conductive. In the illustrated embodiments, the electrode 212 has a conductor 500 (e.g., a wire or trace) extending around a perimeter of the electrode 212. In other embodiments, the conductor 500 may not extend completely around the perimeter of the electrode 212, and may instead extend partially around the perimeter to define an open-loop for the electrode 212. Also, in other embodiments, the electrode 212 may include additional conductor(s) 502 in the space defined by the perimeter of the electrode 212 (FIG. 5E). As shown in the embodiment of FIG. 5E, the electrode 212 has additional conductors 502 extending in the same direction within the perimeter of the electrode 212. Such configuration defines a plurality of openings 260 (e.g., slots) for allowing light to travel therethrough. In other embodiments, the electrode 212 may include additional conductors extending in other directions (such as in a horizontal direction to form a grid of holes with the vertical conductors 502).

It should be noted that the term "opening" (such as the opening 260) may refer to a space without any material that allows light to travel therethrough, or may refer to a material that has at least some optical transparency for allowing light to travel through the material.

Also, in other embodiments, the electrode 212 may be made from a non-transparent conductive material, but is etched with a pattern to allow light to pass therethrough. For example, the electrode may have a polygonal pattern, or any customized pattern, that is etched to allow light to pass therethrough.

In any of the embodiments described herein, the electrode 212 may comprise a chrome layer. Also, in some embodiments, the electrode 212 may comprise Indium tin oxide (ITO), or another transparent conductor.

Returning to FIG. 2, the imaging device 200 further includes a glass substrate 220, wherein the array of detector elements 204 is secured to the glass substrate 220. In the illustrated embodiments, the glass substrate 220 has a first side 222 and an opposite second side 224, wherein the first side 222 is closer to a radiation source than the second side 224. The glass substrate 220 may have a thickness that is less than 2 mm, and more preferably less than 1 mm, and even more preferably less than 0.7 mm. Also, in some embodiments, the substrate 220 that is greater than 0.1 mm, or greater than 0.15 mm. In other embodiments, the glass substrate 220 may have a thickness that is greater than 2 mm. In some embodiments, the array of detector elements 204 is located closer to the first side 222 of the glass substrate 220 than the second side 224. It has been discovered that any blurring effect (due to light traveling from the second scintillator layer 206 through the glass substrate 220 to reach the detector elements 204) is minimal, or does not significantly degrade image quality. Accordingly, the imaging device 200 does not need to have any optical filter coupled between the second scintillator layer 206 and the glass substrate 220 to improve image resolution. However, if improvement is needed, the imaging device 200 may include such optical filter, or may utilize a kernel-based algorithm to improve resolution of the image generated by the imaging device 200.

In other embodiments, the substrate 220 may be made from other materials that are different from glass. For example, in other embodiments, the substrate 220 may be made from plastic.

In other embodiments, the array of detector elements 204 is located closer to the second side 224 of the glass substrate 220 than the first side 222. This configuration is advantageous because the detector elements 204 are in close proximity to the scintillator layer 206, so that photons leaving the scintillator layer 206 can be immediately received by the detector elements 204.

Also, in some embodiments, a first part of the first detector element 204 is located closer to the first side 222 of the glass substrate 220 than the second side 224, and a second part of the first detector element 204 is located closer to the second side 224 of the glass substrate 220 than the first side 222. In other embodiments, both the first part and the second part of the detector element 204 may be located closer to the first side 222 of the glass substrate 220 than the second side 224. In further embodiments, both the first part and the second part of the detector element 204 may be located closer to the second side 224 of the glass substrate 220 than the first side 222.

The scintillator layers 202, 206 may be selectively chosen to fit the required imaging tasks. For example, the first scintillator layer 202 may be copper and Lanex™, while the second scintillator layer 206 may be $CdWO_4$, CsI, or BGO, or vice versa. Also, in some embodiments, GOS with a copper build-up plate may be used for the first scintillator layer 202, the second scintillator layer 206, or both. When implemented in the second scintillator layer 206, the build-up plate may be positioned below the GOS. Scintillator options that are suitable for the first scintillator layer 202 and/or second scintillator layer 206 include, but are not limited to, LKH-5, CdWO4, CsI, with or without build-up plate. The first scintillator layer 202 and the second scintillator layer 206 may be the same or different.

In some embodiments, the first scintillator layer 202 may be non-pixelated, the second scintillator layer 206 may be non-pixelated, or both the first and second scintillator layers 202, 206 may be non-pixelated. In other embodiments, one or both of the first and second scintillator layers 202, 206 may be pixelated.

During use of the imaging device 200, the imaging device 200 is positioned so that the first scintillator layer 202 receives radiation from the radiation source before the second scintillator layer 206. The first scintillator layer 202 receives the radiation, and generates photons in response to the received radiation. The photons are detected by the detector elements 204, which generate electrical signals (imaging signals) in response to the detected photons from the first scintillator layer 202. Some of the radiation is not absorbed by the first scintillator layer 202, and passes through the detector elements 204 and the glass substrate 220, and reaches the second scintillator layer 206. The second scintillator layer 206 receives the radiation and generates photons in response to the received radiation. The photons from the second scintillator layer 206 travel backward towards the direction of the radiation, and reach the detector elements 204. The detector elements 204 generate electrical signals (imaging signals) in response to the photons detected by the respective detector elements 204. Thus, each detector element 204 generates two electrical signals based on photons from the first and second scintillator layers 202, 206. The two electrical signals from each detector element 204 are combined, e.g., via a circuit, to form an image signal for a pixel of an image. The imaging signals may be transmitted to a device, such as a processor for determining an image based on the imaging signals, and/or to a medium for storage.

In order for each detector element 204 to be able to detect photons coming from both the first scintillator layer 202 and the second scintillator layer 206, the detector element 204 needs to be able to detect photons coming from two opposite directions. In some embodiments, the detector element 204 has a photodiode that is configured to detect photons coming from two opposite directions. Alternatively, the detector element 204 may have a first photodiode for detecting photons from the first scintillator layer 202, and a second photodiode for detecting photons from the second scintillator layer 206. The first and second photodiodes may be disposed on the top and bottom sides, respectively, of the detector element 204. Thus, in this embodiment, there are two photodiodes for each pixel, with one of them being upside down. Also, in order for the photons from the second scintillator layer 206 to reach the detector element 204, the electrode 212 is configured to allow light to pass therethrough. For example, the electrode 212 may have one or more opening(s) (like those shown in FIGS. 5A-5C) for allowing light to pass therethrough to reach the detector element 24. Alternatively, or additionally, the electrode 212 may be made from ITO or a combination of ITO with other material, so that the electrode 212 is at least partially transparent. Also, alternatively or additionally, the electrode 212 may be implemented using a thin chrome layer.

The above embodiments illustrate a reverse geometry, which is advantageous because it increases the number of photons that are detected by the detector elements 204. Also, by adding a second scintillator layer 206, the conversion efficiency of the imaging device 200 is improved. In addition, the above approach of using scintillator layers on opposite sides of the detector elements 204 reduces artifacts significantly and does not add significant cost. Furthermore, the above multi-scintillator layers approach is advantageous over an imaging device that utilizes thick non-pixelated scintillator or thick pixelated scintillator. A thick scintillator layer without pixelation will blur the signal and as a consequence, will degrade image resolution. In addition to the blurring, the generated light at the upper part of a thick scintillator layer has to travel a long distance and gets much more attenuated, than the light generated at the lower part of the thick scintillator. Hence, the efficiency does not scale with the thickness. The above approach of using two scintillator layers can be viewed as splitting a thick scintillator layer into two layers, and placing the two scintillator layers on opposite sides of the detector elements 204. This reduces blurring and because the light has to travel a shorter distance, it reduces unwanted light attenuation. Also, thick pixelated scintillators will address the light scattering issue in the thick non-pixelated scintillator as described above, but manufacturing a large area pixelated scintillator is very expensive. Adding a second scintillator layer 206 below the detector elements 204 only adds the cost of a relatively inexpensive second scintillator layer 206. In some embodiments, the substrate 220 is configured to have a thinner thickness that reduces a distance light has to travel from the scintillator layer 206 to the detector elements 204, thereby reducing blurring effect.

In any of the embodiments described herein, the imaging device 200 may not need any optical grid between the first scintillator layer 202 and the detector elements 204, and may also not need any optical grid between the second scintillator layer 206 and the detector elements 204. In other embodiments, the imaging device 200 may optionally further include an optical grid coupled between the first scintillator layer 202 and the detector elements 204, and/or an optical grid coupled between the second scintillator layer 206 and the detector elements 204. The optical grid is configured to allow "on-angle" light generated by the second scintillator 206 to be transmitted towards the detector elements 204, while blocking the "off-angle" light.

Figure 6:
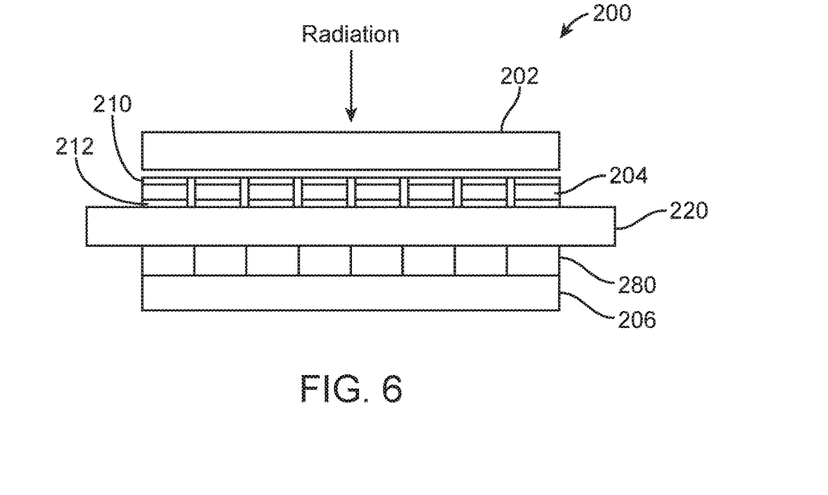
FIG. 6 illustrates another imaging device in accordance with other embodiments.

In some embodiments, the imaging device 200 may further include a layer 280 of focusing elements located between the array of detector elements 204 and the second scintillator layer 206 (FIG. 6). The layer 280 of focusing elements is configured to direct light generated by the second scintillator 206 to reach the detector elements 204, thereby improving the resolution of the image. The layer 280 of focusing elements may comprise a fiber optic array, a brightness enhancement film (BEF), an optical grid, an optical filter, or any optical device that is capable of channeling optical rays (e.g., using Fresnel refraction and/or reflection). In other embodiments, the focusing elements are not needed, and the imaging device 200 does not include the focusing elements between the detector elements 204 and the second scintillator layer 206.

Figure 7:
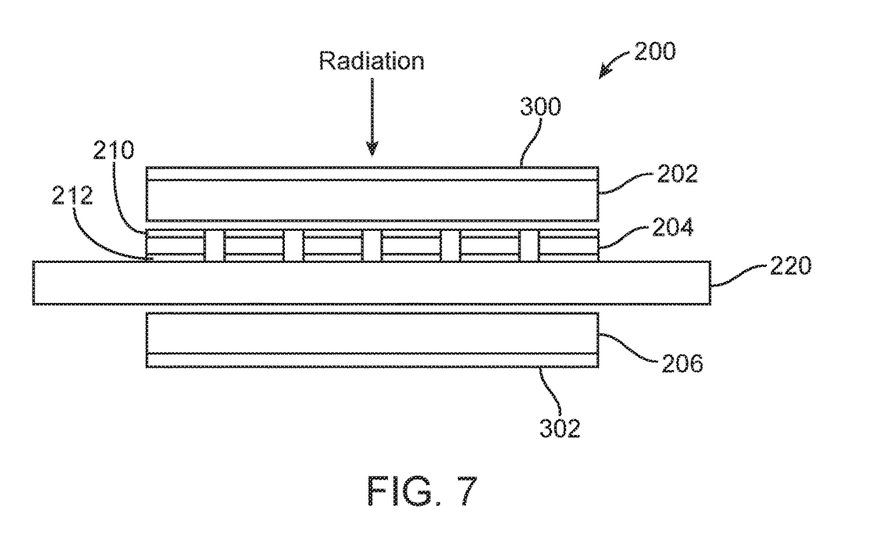
FIG. 7 illustrates another imaging device in accordance with other embodiments.

In some embodiments, the imaging device 200 may optionally further include a first plate 300 coupled to the first scintillator layer 202, and a second plate 302 coupled to the second scintillator layer 206, wherein both the first scintillator layer 202 and the second scintillator layer 206 are between the first and second plates 300, 302 (FIG. 7). During use, radiation may interact with the first plate 300 and the second plate 302 (in addition to the first and second scintillator layers 202, 206) to create photons for detection by the detector elements 204.

One consideration in maximizing signal-to-noise ratio (SNR) is equalizing the signals from the first and second scintillator layers 202, 206. Signal detection theory dictates that the electron signal amplitude from each side's scintillator (after conversion of the optical signal by the photodiode) should be proportional to that side's scintillator's detective quantum efficiency (DQE). For example, if the same scintillator with the same thickness is used for the top and bottom sides, but the photodiode efficiency on the bottom side is, for example, ½ of the efficiency of the top side, then a ½× neutral density filter may be put between the top scintillator and the detector elements 204 to equalize the signals, or to at least bring them closer to each other. Alternatively, different scintillators with different optical yields may be used on the top and bottom sides.

In some embodiments, the first electrical signal (generated based on light from the first scintillator layer 202) may have a first feature value (e1), and the second electrical signal (generated based on light from the second scintillator layer 206) may have a second feature value (e2). The first and second feature values may be first and second electron signal amplitudes, respectively. The ratio, min (e1, e2)/max (e1, e2), may be larger than a threshold. For examples, the threshold may be larger than 0.5, larger than 0.7, larger than 0.9, etc. In any of the examples, the threshold may be less than or equal to 1.0. In some embodiments, such ratio may be achieved to be below the prescribed threshold by selecting the appropriate materials and thicknesses for the first and second scintillator layers 202, 206. In other embodiments, the imaging device 200 may optionally further include a first neutral density filter located between the first scintillator layer 202 and the first detector element, and/or a second neutral density filter located between the second scintillator layer 206 and the first detector element. The first neutral density filter and/or the second neutral density filter may be configured to improve a signal-to-noise ratio of the imaging device. For example, the first neutral density filter and/or the second neutral density filter may be configured such that min (e1, e2)/max (e1, e2) is larger than a threshold.

In some embodiments, a signal-to noise ratio of the imaging device 202 is based on (1) respective quantum efficiencies (QE1,QE2) of the first and second scintillator layers 202, 206, (2) respective detective quantum efficiencies (DQE1,DQE2) of the first and second scintillator layers 202, 206, (3) respective optical yields (☐☐☐☐☐☐☐of the first and second scintillator layers 202, 206, (4) optical sensitivities (p1, p2) of the detector element(s) associated with the first and second scintillators respectively 202, 206, or (5) a combination of any of the foregoing.

Also, in some embodiments, the first feature value (e1) may be a function of quantum efficiency QE1 of the first scintillator layer 202, optical yield ☐☐ of the first scintillator layer 202, and optical sensitivity p1 of the detector element(s) associated with the first scintillator layer 202. Also, the second feature value (e2) may be a function of quantum efficiency QE2 of the second scintillator layer 206, optical yield ☐☐ of the second scintillator layer 206, and optical sensitivity p2 of detector element(s) associated with the second scintillator layer 206.

In other embodiments, the first feature value (e1) may be a function of detective quantum efficiency DQE1 of the first scintillator layer, optical yield☐☐☐ of the first scintillator layer, and optical sensitivity p1 of the detector element(s) associated with the first scintillator layer. Also, the second feature value (e2) may be a function of detective quantum efficiency DQE2 of the second scintillator layer, optical yield☐☐☐ of the second scintillator layer, and optical sensitivity p2 of the detector element(s) associated with the second scintillator layer.

It should be noted that the term "first scintillator layer" and the term "second scintillator layer" need not refer to the top scintillator layer and the bottom scintillator layer, respectively. For example, in other cases, the first scintillator layer may refer to the bottom scintillator layer, and the second scintillator layer may refer to the top scintillator layer.

It should be noted that the embodiments of the imaging device 200 described herein are not limited to portal imagers, and that any of the embodiments of the imaging device 200 described herein may be used with diagnostic radiation beam. The imaging device 200 may be a part of a treatment machine, a part of an imaging machine, or both.

In the above embodiments, various features have been described with reference to medical imaging. In other embodiments, any or all of the features described herein may be implemented for security applications. For example, in some embodiments, any of the imaging devices 200 described herein may be employed for cargo screening.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An imaging device, comprising:
a first scintillator layer;
an array of detector elements, wherein the array of detector elements comprises a first detector element;
a second scintillator layer, wherein the array of detector elements is located between the first scintillator layer and the second scintillator layer; and
a first neutral density filter located between the first scintillator layer and the first detector element and/or a second neutral density filter located between the second scintillator layer and the first detector element;
wherein the first detector element is configured to generate a first electrical signal in response to light from the first scintillator layer, and to generate a second electrical signal in response to light from the second scintillator layer;
wherein the imaging device further comprises a first plate coupled to the first scintillator layer, and/or a second plate coupled to the second scintillator layer; and
wherein the first plate and/or the second plate is configured to provide photons.

2. The imaging device of claim 1, wherein the first neutral density filter and/or the second neutral density filter is configured to improve a signal-to-noise ratio of the imaging device.

3. The imaging device of claim 1, wherein a signal-to noise ratio of the imaging device is based on (1) respective quantum efficiencies (QE1,QE2) of the first and second scintillator layers, (2) respective detective quantum efficiencies (DQE1,DQE2) of the first and second scintillator layers, (3) respective optical yields ($\alpha 1$, $\alpha 2$) of the first and second scintillator layers, (4) optical sensitivities (p1, p2) of the first detector element associated with the first and second scintillators respectively, or (5) a combination of any of the foregoing.

4. The imaging device of claim 1, wherein the second scintillator layer is configured to receive radiation after it has passed through the array of detector elements.

5. The imaging device of claim 1, further comprising a first electrode situated between the first scintillator and the first detector element, wherein the first electrode is configured to allow light from the first scintillator layer to reach the first detector element.

6. The imaging device of claim 5, further comprising a second electrode configured to allow the light from the second scintillator layer to reach the first detector element.

7. The imaging device of claim 6, wherein the second electrode is at least partially transparent to light.

8. The imaging device of claim 6, wherein the second electrode comprises a first opening for allowing the light from the second scintillator layer to pass therethrough.

9. The imaging device of claim 8, wherein the second electrode comprises a second opening.

10. The imaging device of claim 8, wherein the first opening comprises a circular opening, a square opening, a rectangular opening, or a slot.

11. The imaging device of claim 8, wherein the second electrode has a ring configuration.

12. The imaging device of claim 8, wherein the second electrode has a grid configuration, and the first opening is one of a plurality of grid holes.

13. The imaging device of claim 6, wherein the second electrode comprises a chrome layer.

14. The imaging device of claim 6, wherein the second electrode comprises ITO or another transparent conductor.

15. The imaging device of claim 6, wherein the first detector element comprises a hardware component, and wherein the second electrode and the hardware component are in a side-by-side configuration.

16. The imaging device of claim 15, wherein the second electrode comprises a conductor extending along at least a part of a periphery of the second electrode, and one or more optical openings surrounded by the periphery.

17. The imaging device of claim 16, wherein the second electrode further comprises one or more additional conductors extending within a space that is surrounded by the periphery of the second electrode.

18. The imaging device of claim 15, wherein the hardware component comprises at least a part of a thin-film-transistor (TFT).

19. The imaging device of claim 1, wherein the first detector element has a first part configured to generate the first electrical signal in response to the light from the first scintillator layer, and a second part configured to generate the second electrical signal in response to the light from the second scintillator layer.

20. The imaging device of claim 19, wherein the first part is a top side of the first detector element, and the second part is a bottom side of the first detector element.

21. The imaging device of claim 19, wherein the first part comprises a first photodiode, and the second part comprises a second photodiode, and wherein the first photodiode and the second photodiode form a side-by-side configuration.

22. The imaging device of claim 1, further comprising a substrate, wherein the array of detector elements is secured to the substrate, wherein the substrate has a first side and an opposite second side, the first side being closer to a radiation source than the second side.

23. The imaging device of claim 22, further comprising a layer of focusing elements located between (1) the array of detector elements and (2) the first scintillator layer or the second scintillator layer.

24. The imaging device of claim 22, further comprising an optical grid coupled to the first scintillator layer or the second scintillator layer.

25. The imaging device of claim 22, wherein the substrate has a thickness that is less than 2 mm.

26. The imaging device of claim 1, further comprising a first optical grid coupled to the first scintillator layer, and a second optical grid coupled to the second scintillator layer.

27. The imaging device of claim 1, comprising both the first plate and the second plate, wherein both the first scintillator layer and the second scintillator layer are between the first and second plates.

28. An imaging device, comprising:
a first scintillator layer;
an array of detector elements, wherein the array of detector elements comprises a first detector element;
a second scintillator layer, wherein the array of detector elements is located between the first scintillator layer and the second scintillator layer; and
a first neutral density filter located between the first scintillator layer and the first detector element and/or a second neutral density filter located between the second scintillator layer and the first detector element;
wherein the first detector element is configured to generate a first electrical signal in response to light from the first scintillator layer, and to generate a second electrical signal in response to light from the second scintillator layer;
wherein the first electrical signal has a first feature value (e1), and the second electrical signal has a second feature value (e2); and
wherein the first neutral density filter and/or the second neutral density filter is configured such that min (e1, e2)/max (e1, e2) is larger than a threshold.

29. The imaging device of claim 28, wherein the first feature value (e1) is a function of quantum efficiency QE1 of the first scintillator layer, optical yield $\alpha 1$ of the first scintillator layer, and optical sensitivity p1 of the first detector element associated with the first scintillator layer; and
wherein the second feature value (e2) is a function of quantum efficiency QE2 of the second scintillator layer, optical yield $\alpha 2$ of the second scintillator layer, and optical sensitivity p2 of the first detector element associated with the second scintillator layer.

30. The imaging device of claim 28, wherein the first feature value (e1) is a function of detective quantum efficiency DQE1 of the first scintillator layer, optical yield $\alpha 1$ of the first scintillator layer, and optical sensitivity p1 of the first detector element associated with the first scintillator layer; and
wherein the second feature value (e2) is a function of detective quantum efficiency DQE2 of the second scintillator layer, optical yield $\alpha 2$ of the second scintillator layer, and optical sensitivity p2 of the first detector element associated with the second scintillator layer.

31. The imaging device of claim 28, wherein the threshold is larger than 0.5.

32. The imaging device of claim 28, wherein the threshold is larger than 0.7.

* * * * *